United States Patent [19]

Tansey

[11] Patent Number: 5,406,957
[45] Date of Patent: Apr. 18, 1995

[54] ELECTROENCEPHALIC NEUROFEEDBACK APPARATUS FOR TRAINING AND TRACKING OF COGNITIVE STATES

[76] Inventor: Michael A. Tansey, 194 Bywater, Somerville, N.J. 08876

[21] Appl. No.: 121,373

[22] Filed: Sep. 14, 1993

Related U.S. Application Data

[63] Continuation of Ser. No. 940,190, Sep. 3, 1992, abandoned, which is a continuation-in-part of Ser. No. 831,182, Feb. 5, 1992, abandoned.

[51] Int. Cl.⁶ .............................................. A61B 5/00
[52] U.S. Cl. ................................... 128/732; 128/731; 364/413.05
[58] Field of Search ................... 128/731, 732, 746; 364/413.03, 413.02, 572, 576, 413.04, 413.05, 413.13, 413.2

[56] References Cited

U.S. PATENT DOCUMENTS

| | | | |
|---|---|---|---|
| 3,855,998 | 12/1974 | Hidalgo-Briceno | 128/732 |
| 3,978,847 | 9/1976 | Fehmi et al. | 128/732 |
| 4,140,997 | 2/1979 | Brady | 340/148 |
| 4,332,566 | 6/1982 | Mazeski et al. | 434/178 |
| 4,498,080 | 2/1985 | Culver | 340/728 |
| 4,736,751 | 4/1988 | Gevins et al. | 128/732 |
| 4,800,895 | 1/1989 | Moberg et al. | 128/731 |
| 4,846,190 | 7/1989 | John | 128/731 |
| 4,883,067 | 11/1989 | Knispel et al. | 128/732 |
| 4,919,143 | 4/1990 | Ayers | 128/732 |
| 4,926,969 | 5/1990 | Wright et al. | 128/731 |
| 4,928,704 | 5/1990 | Hardt | 128/732 |
| 4,979,110 | 12/1990 | Albrecht et al. | 364/413.03 |
| 5,024,235 | 6/1991 | Ayers | 128/732 |
| 5,320,109 | 6/1994 | Chamoun et al. | 128/731 |

FOREIGN PATENT DOCUMENTS

| | | | |
|---|---|---|---|
| 375106 | 6/1990 | European Pat. Off. | 128/732 |
| 8303745 | 11/1983 | WIPO | 128/731 |

OTHER PUBLICATIONS

Silverman et al, "A Hybrid Broad-Band ... Experiments" *IEEE Trans. on Biomedical Engineering*, vol. BME-20, No. 1, Jan. 1973, pp. 60–62.

Bricolo. "Automatic Detection of Sleep Spindles ... Components" *Med. and Biol. Engng.* vol. 8, No. 5, pp. 517–519 (1970).

*Primary Examiner*—Stephen C. Pellegrino
*Assistant Examiner*—Guy V. Tucker
*Attorney, Agent, or Firm*—Mathews, Woodbridge & Collins

[57] ABSTRACT

A biofeedback system provides measurement of bioelectric signals in up to about a 1 hertz window of particular bandwidths. A bioelectric signal is amplified by a preamplifier. The composite amplitude of the signal is determined by performing a fast Fourier transform on the amplified signal. Particular bandwidths can be displayed and monitored on a computer. The display permits training of the person being monitored with audio or verbal feedback.

12 Claims, 7 Drawing Sheets

ELECTROENCEPHALIC NEUROFEEDBACK APPARATUS FOR TRAINING AND TRACKING OF COGNITIVE STATES

CROSS REFERENCE TO RELATED APPLICATION

This application is a continuation of U.S. patent application entitled: ELECTROENCEPHALIC NEUROFEEDBACK APPARATUS AND METHOD METHODS FOR TRAINING AND TRACKING OF COGNITIVE STATES, Ser. No. 07/940,190, filed Sep. 3, 1992 abandoned which is a continuation in part of U.S. patent application entitled: THE TANSEY TECHNIQUE AND TRAINING SYSTEM: ELECTROENCEPHALIC NEUROFEEDBACK APPARATUS, PROCEDURE AND METHOD FOR THE TRACKING AND TRAINING OF COGNITIVE STATES AND THE REMISSION OF DISORDERS CHARACTERIZED BY CEREBRAL DYSFUNCTION, Ser. No. 831,182, filed Feb. 5, 1992, now abandoned, the entire text and contents of which are incorporated by reference into this application.

BACKGROUND OF THE INVENTION

1. Field of the Invention

The invention relates to an apparatus and method for monitoring, analyzing and utilizing brainwave data.

2. Description of the Related Art

The human brain can be viewed as functionally interrelated synaptic pathways and neural activation matrices. These pathways and matrices are predisposed to functionally respond and further develop with use. This is the basis for all higher learning. At any given moment, the brain radiates a plethora of events, tasks and states which are related to neural discharge patterns. Neural discharge patterns can be defined as brainwave signatures. A brainwave signature can be associated with human cognitive states, learning, intellectual ability and disability.

Considerable research has been directed to biological feedback of brainwave signals known as electroencephalogram (EEG) signals. One conventional neurophysiological study established a functional relationship between behavior and bandwidths in the 12-15 Hz range relating to sensorimotor cortex rhythm EEG activity (SMR). Sterman, M. B., Lopresti, R. W., & Fairchild, M. D. (1969). Electroencephalographic and behavioral studies of monomethylhdrazine toxicity in the cat. *Technical Report AMRL-TR*-69 3, Wright-Patterson Air Force Base, Ohio, Air Systems Command. A cat's ability to maintain muscular calm, explosively execute precise, complex and coordinated sequences of movements and return to a state of calm was studied by monitoring a 14 cycle brainwave. The brainwave was determined to be directly responsible for the suppression of muscular tension and spasm. It was also demonstrated that the cats could be trained to increase the strength of specific brainwave patterns associated with suppression of muscular tension and spasm. Thereafter, when the cats were administered drugs which would induce spasms, the cats which were trained to strengthen their brainwaves were resistent to the drugs.

The 12-15 Hz SMR brainwave band has been used in conventional EEG biofeedback training for rectifying pathological brain underactivation. In particular the following disorders have been treated using biofeedback training: epilepsy (as exemplified in M. B. Sterman's, M. B. 1973 work on the "Neurophysiologic and Clinical Studies of Sensorimotor EEG Biofeedback Training: Some Effects on Epilepsy" L. Birk (Ed.), *Biofeedback: Behavioral Medicine*, New York: Grune and Stratton); Giles de la Tourette's syndrome and muscle tics (as exemplified in the inventor's 1986 work on "A Simple and a Complex Tic (Giles de la Tourette's Syndrome): Their response to EEG Sensorimotor Rhythm Biofeedback Training", *International Journal of Psychophysiology*, 4, 91-97 (1986)); hyperactivity (described by M. N. Shouse, & J. F. Lubar's in the work entitled "Operant Conditioning of EEG Rhythms and Ritalin in the Treatment of Hyperkinesis", *Biofeedback and Self-Regulation*, 4, 299-312 (1979); reading disorders (described by M. A. Tansey, & Bruner, R. L.'s in "EMG and EEG Biofeedback Training in the Treatment of a 10-year old Hyperactive Boy with a Developmental Reading Disorder", *Biofeedback and Self-Regulation*, 8, 25-37 (1983)); learning disabilities related to the finding of consistent patterns for amplitudes of various brainwaves (described in Lubar, Bianchini, Calhoun, Lambert, Brody & Shabsin's work entitled "Spectral Analysis of EEG Differences Between Children with and without Learning Disabilities", *Journal of Learning Disabilities*, 18, 403-408 (1985)) and; learning disabilities (described by M. A. Tansey in "Brainwave signatures—An Index Reflective of the Brain's Functional Neuroanatomy: Further Findings on the Effect of EEG Sensorimotor Rhythm Biofeedback Training on the Neurologic Precursors of Learning Disabilities", *International Journal of Psychophysiology*, 3, 85-89 (1985)). In sum, a wide variety of disorders, whose symptomology includes impaired voluntary control of one's own muscles and a lowered cerebral threshold of overload under stress, were found to be treatable by "exercising" the supplementary and sensorimotor areas of the brain.

Conventional EEG biofeedback methods and apparatus have referenced brainwave activity in terms of large bands of EEG. As such, brainwave activity has traditionally been classified as follows: delta waves lie in the frequency range of 0 to 3.5 Hz; theta waves lie in the frequency range of 4 to 7 Hz; alpha waves lie in the frequency range of 8 to 13 Hz; beta waves lie in the frequency range above 13 HHz; and sensorimotor rhythm (SMR) waves lie in the frequency range of 12 to 15 Hz. Several patents have been directed to monitoring EEG in terms of the sensed amplitudes and percentages of alpha, theta, beta, delta and SMR waves.

U.S. Pat. No. 4,928,704 describes a biofeedback method and system for training a person to develop useful degrees of voluntary control of personal EEG activity. EEG sensors are attached to cortical sites on a head of a person for sensing EEG energy. EEG electrical energy is filtered into the pre-defined sub-bands of alpha, theta, beta and delta. Other patents directed to EEG biofeedback with alpha, theta, beta, delta and SMR waves include U.S. Pat. Nos.: 3,855,988; 4,140,997; 4,883,067; 4,919,143; 5,024,235 and European Patent No. 375,106.

U.S. Pat. No. 4,746,751 describes a system for displaying multichannel EEG data. In performing this, the procedure and method entails Evoked Response Potential signal averaging. A summed signal averaged brain map may be pieced together being comprised of reflections of the average amount of overall energy monitored over many electrode sites. In ERP, the subject receives a set of stimuli which evoke brainwaves. Other examples of patents directed to ERP include U.S. Pat. Nos.: 4,498,080; 4,926,969 and PCT Patent Application No. 8303745.

U.S. Pat. No. 4,926,969 ('969) was cited in the inventor's parent application Ser. No. 831,182. The '969 patent describes a sensory drive controller designed to detect evoked response potentials as a result of stimuli presented to the person. EEG signals taken from the subject at electrodes are amplified and filtered to enhance averaging and correlation procedures for establishing an ERP template. The ERP template is compared with detected evoked response potentials to determine the degree of similarity between the two signals.

A major disadvantage in the conventional EEG biofeedback studies has been the poor resolution of brainwave bands produced by conventional bandpass filters used as a front end for signal processing electronics. Another drawback has been that the bandpass filters are easily overloaded by an upsurge of electrical energy or high amplitude slow waves. An upsurge of electrical energy accompanies muscle movement and high amplitude slow waves activity accompanies many cerebral disorders. These unwanted, and all too frequent, signal contaminating sources are referred to as artifacts. Bandpass analysis is dependent on differential preamplifiers which multiply many thousands of times (i.e., as much as 50,000 times) the biologic signals and any accompanying artifacts. Such electronic/mechanical signal refiners contribute to inaccuracy in the monitoring of EEG signals.

Another disadvantage in conventional mechanical bandpass filtering is that arbitrary and inexact bandwidths are used to train specific brainstates. An exact analysis of waveforms is essential to EEG biofeedback protocols. Additional drawbacks to conventional systems is their reliance on multiplexors which may sample the bandpass configured signal at a rate of one sampling per second of time. For example, when monitoring a 14 cycle per second wave form 14 Hz signal, only one component will be measured, thus 13 of the 14 components of the waveform are missed. The prior art also has the disadvantage of being limited to delta, theta, alpha, beta and SMR representations.

A system for simultaneously monitoring and manipulating waveforms in a continuum from 0 to 90 Hz is not found in the prior art.

SUMMARY OF THE INVENTION

Briefly described, the invention comprises a system for monitoring and manipulating bioelectric and biofeedback data in a range of about 0 to about 90 hertz. The system typically includes displaying waveforms in 1 hertz or less windows.

In a preferred embodiment, an active electrode is mounted along the midline of the skull of the person. A reference electrode and a ground electrode are placed on opposite ears of the person. Bioelectric EEG signals of the person are detected by the active electrode, reference electrode, and ground electrode. A preamplifier amplifies and optically isolates the detected bioelectric signals. The amplified data is transmitted to a signal processor. Preferably, the signal processor is a digital signal processor of a computer. A computer useful in practice of the present invention is manufactured by NeXT, Inc., as NeXT ® Station. NeXT ® is a registered trademark of NeXt Computer, Inc.

The signal processor performs a fast Fourier transform on the amplified bioelectric signal to determine the amplitude of the bioelectric signal. Biofeedback software allows the user to monitor bioelectric bandwidths of interest from the detected bioelectric signals. A window of 1 hertz or less is the bioelectric bandwidth of interest. For example, if the user chooses to monitor a bioelectric bandwidth of 14 hertz, the window will be from about 13.5 hertz to about 14.5 hertz. The amplitude of the bioelectric signal related to the bandwidth of interest can be displayed in a first window of a computer display. Also, an average value of the amplitude of the bioelectric signal over time can be displayed in a second window of the computer display. The amplitudes of the bandwidths of interest over time of the sessions are stored in the memory of the computer so that a monitoring session can be replayed. Also, detected amplitudes for all bandwidths in the 0 to 90 hertz bandwidth can be stored in the memory of the computer workstation.

Biofeedback training is performed by observing the displayed amplitudes of the bandwidths of interest and providing verbal or musical feedback to the user in response to changes in the observed displayed amplitudes.

DETAILED DESCRIPTION OF THE INVENTION

During the course of this description like numbers will be used to identify like elements according to the different figures which illustrate the invention.

Figure 1:
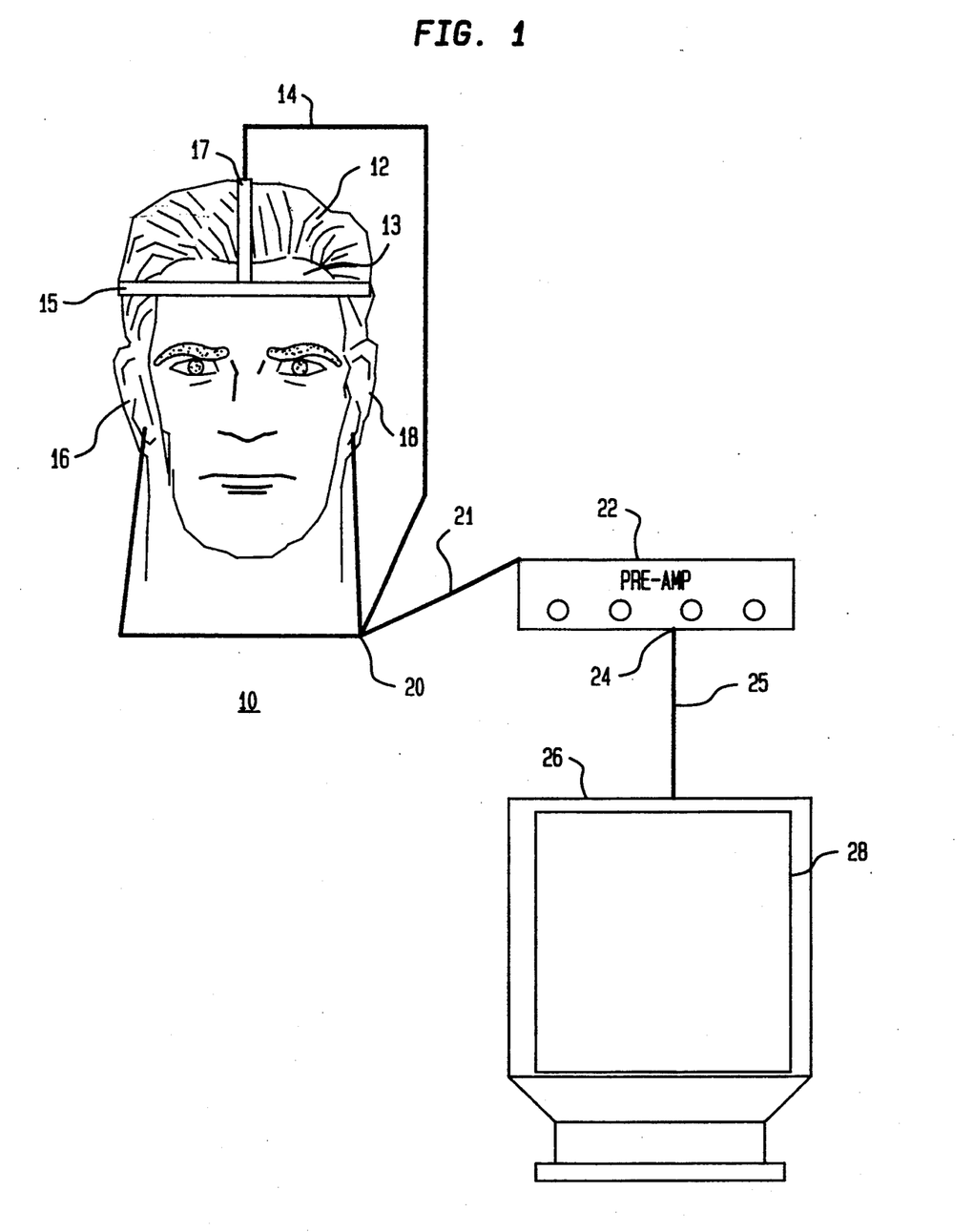
FIG. 1 is a schematic diagram of the system in accordance with the present invention.

FIG. 1 is a schematic diagram of an EEG biofeedback system 10 in accordance with the present invention. In a preferred embodiment, a person 12 is monitored with three electrodes. Active electrode 14 is mounted as comfortably as possible along the midline of the skull of person 12. Reference electrode 16 is placed on one ear of person 12 and ground electrode 18 is placed on the other ear of person 12. Preferably reference electrode 16 and ground electrode 18 are attached with earclips. Active electrode 14 preferably has a contact surface with a length of about 6.5 cm and a width of about 1.3 cm. It will be appreciated to those skilled in the art that other sizes and shapes of electrodes can be used with the teachings of the present invention.

Active electrode 14 is preferably placed lengthwise along the midline of the top of the skull to overlay the cerebral longitudinal fissure of person 12. A first band 15 is placed around the head parallel to the eyebrows and across the middle of the forehead 13 of person 12. A second band 17 is placed across the top of the head of person 12 and attaches to first band 15. Preferably first band 15 and second band 17 are formed of an elastic material. In the alternative, active electrode 16 can be part of a headphone device with reference electrode 16 and ground electrode 18 incorporated into the earphones of the headphone device. It will be understood by those skilled in the art that types and arrangement of electrodes can be used. For example, multiple sensors can be placed along multiple areas of the brain.

Bioelectric signals 20 detected by active electrode 14, reference electrode 16 and ground electrode 18 can be defined as raw EEG data of person 12. Bioelectric signals 20 are applied by line 21 to preamplifier 22. Bioelectric signals 20 can be in the range from about 0 to about 90 hertz. In an alternative arrangement, bioelectric signals 20 can be remotely transmitted to preamplifier 22 by a radio frequency transmitter. The radio frequency transmitter can be attached to first band 15. This remote transmitter has the advantage of allowing free movement of patient 12 during monitoring of bioelectric signals 20. Preamplifier 22 amplifies and optically isolates bioelectric signals 20. Preferably preamplifier 22 amplifies bioelectric signals 20 by a factor of about 10 to about 100. An example of a pre-amplifier useful for practice of this invention is manufactured by Biofeedback Systems as Medical Pre-Amplifier Model PA-2M.

Figure 2:
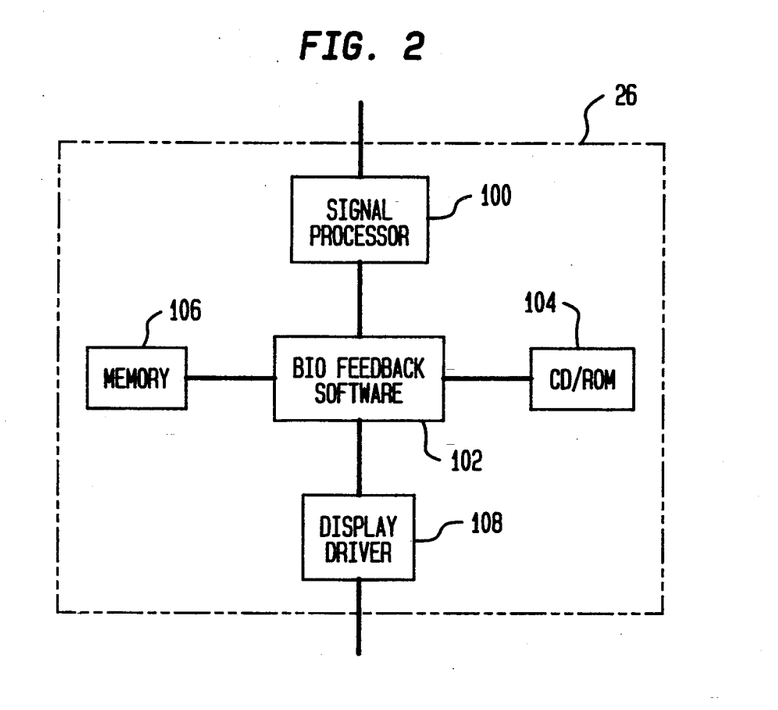
FIG. 2 is a schematic diagram of the computer system in accordance with the present invention.

Amplified signal 24 is applied by line 25 to a signal processor 100 of computer workstation 26 as shown in FIG. 2. Signal processor 100 performs a fast Fourier transform (FFT) on amplified signal 24 for determining the amplitude of the signal. The amplitude of the bioelectric signal is defined in microvolts. The processed bioelectric signals can be defined as brainwave signatures. A computer workstation useful for practice of this invention is manufactured by NeXT, as the NeXT station computer. The NeXT station includes a digital signal processor using fast Fourier transforms. The FFT computation can be carried out in the computer workstation in real time. The composite amplitude of the signal is determined by performing a fast Fourier transform on the amplified signal. A frequency window of up to about 1 hertz around a frequency defines a bioelectric frequency band. Sampling of bioelectric signals 12 by computer workstation 26 is performed at a rate of about 8,000 samples per second.

Biofeedback software 102 of computer workstations 26 provides selection of bandwidths of interest from the detected bioelectric signals 20. A display driver 108 interacts with biofeedback software 102 to display particular bandwidths of interest on computer screen 28. Preferably computer screen 28 is updated in one second intervals with the continued detection of bioelectric signals 20. An example of biofeedback software, useful for practice of the present invention is manufactured by In Sync Institute Inc., as EEG Brainwave Analysis Program Digital readings for each bandwidth varying peak-to-peak microvolt value are displayed on computer 28.

The amplitude values calculated from signal processor 100 related to the bandwidths of interest can be stored by biofeedback software 102 in computer memory 106. Amplitude values can be stored over time for an entire session of brainwave monitoring. In an alternative arrangement all amplitude values calculated for the range of 0 to 90 hertz can be stored in computer memory 106.

Biofeedback software 102 interacts with CD sound system 104 of computer workstation 26. CD sound system 104 can be used in training person 12, as described with reference to the following drawings. A CD sound system is included in the NeXT station.

Figure 3:
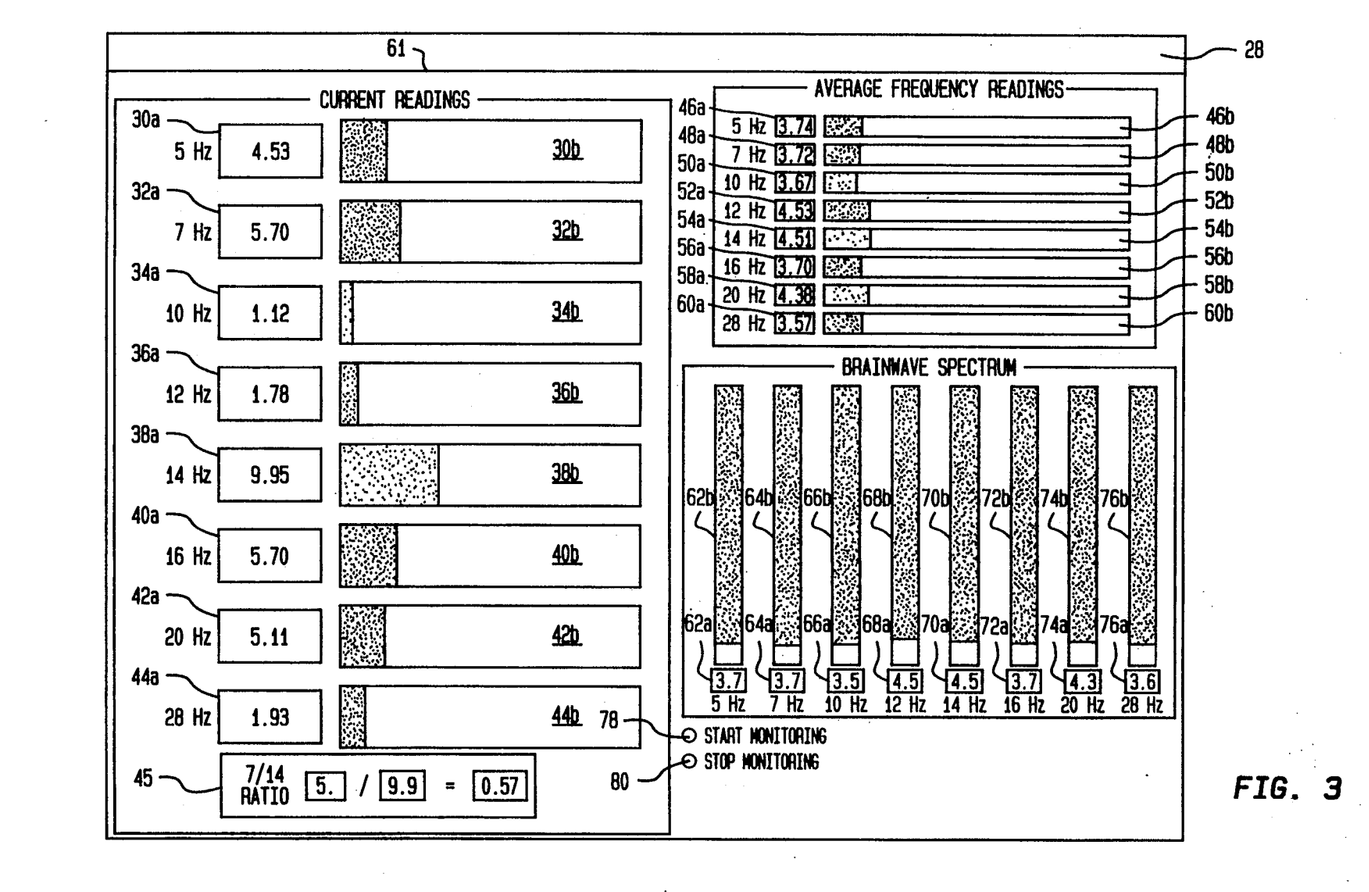
FIG. 3 is a front view of the display of the present invention for a "heavy hands" condition.

FIG. 3 illustrates a display 61 of a particular brainwave signature. This brainwave signature relates to a "heavy hands" condition of person 12. To achieve the "heavy hands" condition person 12 is asked to concentrate on feeling that they have heavy hands. Bandwidths of 5 Hz, 7 Hz, 10 Hz, 12 Hz, 14 Hz, 16 Hz and 28 Hz were chosen to be of interest. Monitoring of patient 12 with biofeedback software 102 is started by having a user click a mouse on the start monitoring window 78 and the monitoring of patient 12 is stopped by having a user click a mouse in the stop monitoring window 80 of display 61. An amplitude for a 1 hertz window for each bandwidth was calculated with a FFT, as described above. In Computer screen 28 displays changes in EEG/energy/amplitudes across eight bandwidths so that a trainer can act on these changes. Display 61, bandwidths of 5 Hz, 7 Hz, 10 Hz, 12 Hz, 14 Hz, 16 Hz, 20 Hz and 28 Hz are displayed in respective windows 30a-b, 32a-b, 34a-b, 36a-b, 38a-b, 40a-b, 42a-b and 44a-b. The amplitude of each of the bandwidths is displayed in a first portion window 30a, 32a, 34a, 36a, 39a, 40a, 42a and 44a and a bar graph of the amplitude is displayed a second window 30b, 32b, 34b, 36b, 38b, 40b, 42b and 44b. A value of the average amplitude for each band is displayed in windows 46a-b, 48a-b, 50a-b, 52a-b, 54a-b, 56a-b, 58a-b and 60a-b. Windows 62a-b, 64a-b, 68a-b, 70a-b, 72a-b, 74a-b and 76a-b indicate the average amplitude of the brainwave signature. Display 61 indicates that a "heavy hands" condition causes an increased value for the 14 hz bandwidths than for the other displayed bandwidths.

Figure 4:
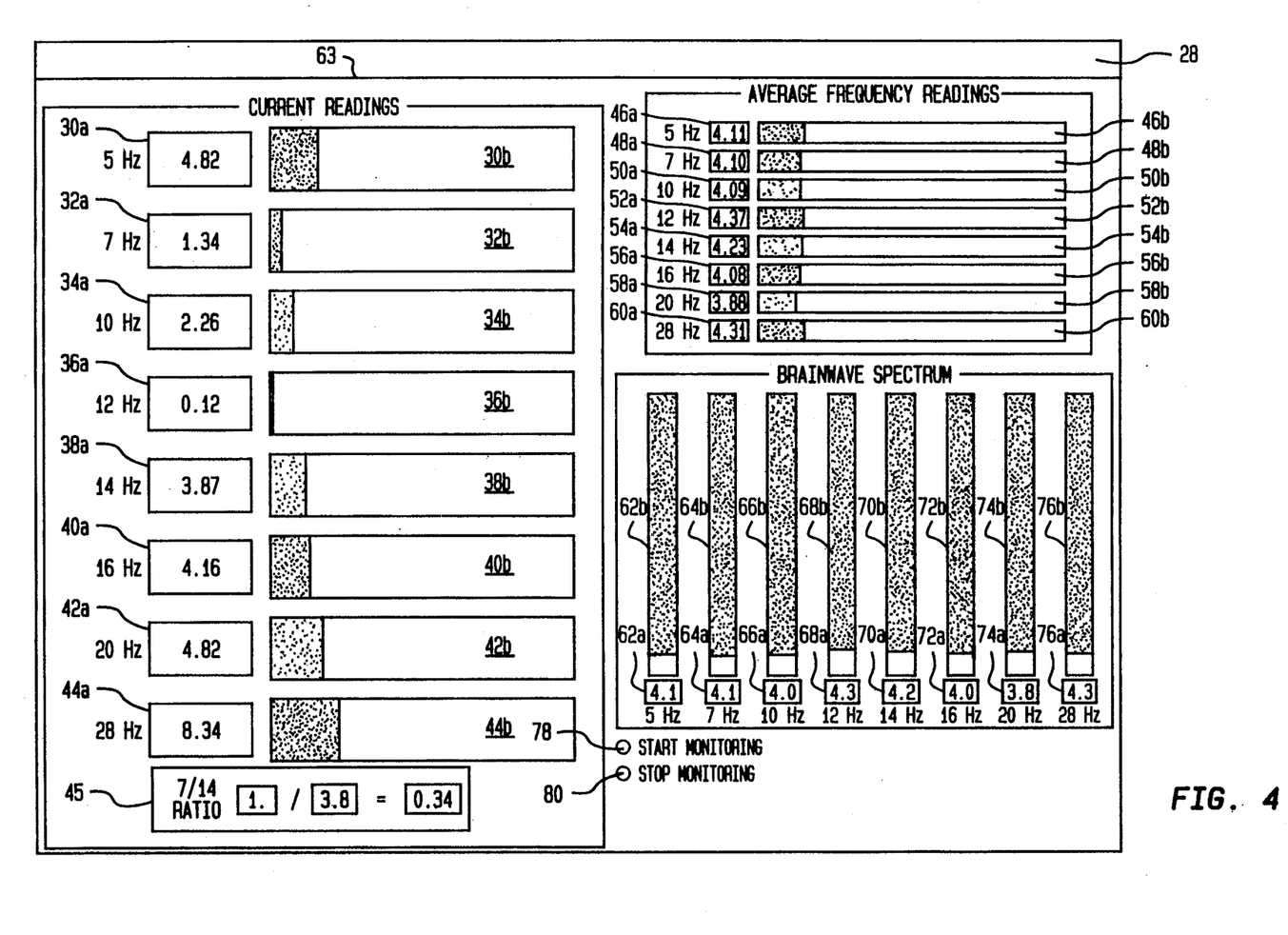
FIG. 4 is a front view of the display of the present invention for a "warm hands" condition.
Figure 5:
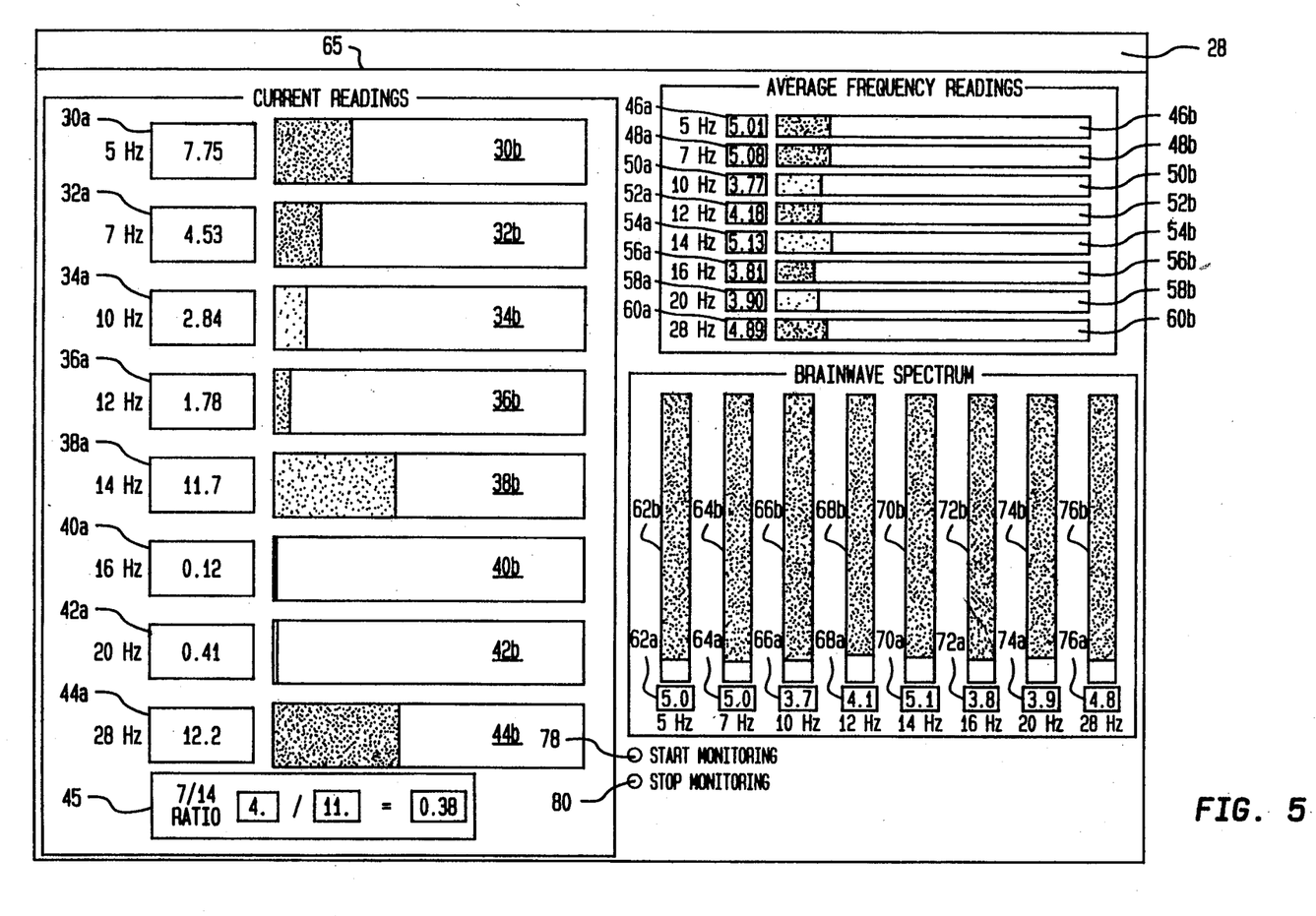
FIG. 5 is a front view of the display of the present invention for a "heavy warm hands" condition.

Display 63 illustrates a brainwave signature related to a "warm hands" condition of patient 12, as shown in FIG. 4. Display 63 shows that a "warm hands" condition causes an increased value for the 28 hertz bandwidths. Display 65, shown in FIG. 5, illustrates a brainwave signature related to a "heavy, warm hand" condition of person 12. In this condition, person 12 is asked to concentrate on the feeling of having "heavy warm hands". Display 63 shows increased values for the 14 hertz and 28 hertz bandwidths.

Figure 6:
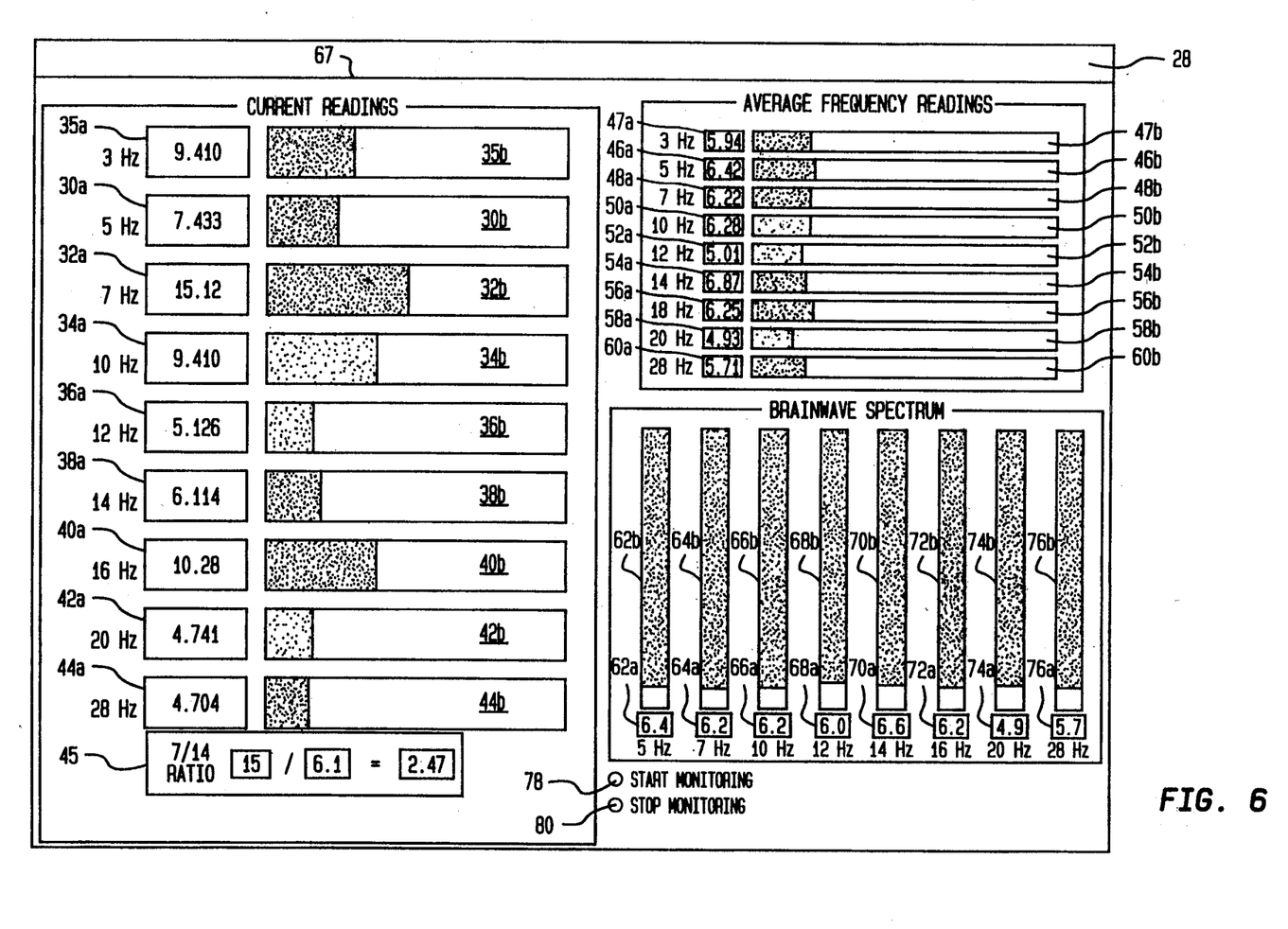
FIG. 6 is a front view of a display of the present invention for a "happy" condition.

Display 67 illustrates a brainwave signature for a condition of "being happy", as described in FIG. 6. The "being happy" condition shows increased values in the 3 hz, 7 hz and 16 hz bandwidths.

From the brainwave signature displays 61, 63, 65 and 67 it is shown that monitoring of the muscular system with the condition of "heavy hands" increases the 14 hz bandwidths; monitoring the vascular system with the condition of "warm hands" increases the 28 hz window; and monitoring the emotional system with the condition of being "happy" increases the 7 hz, 10 hz and 16 hz bandwidths. Displays 61, 63, 65, 67 and 69 can include a ratio of two wavelengths. For example, a "7/14" ratio is displayed in window 45. A ratio of less than one indicates a higher value of the 14 hz bandwidth than for the 7 hz bandwidths.

Figure 7:
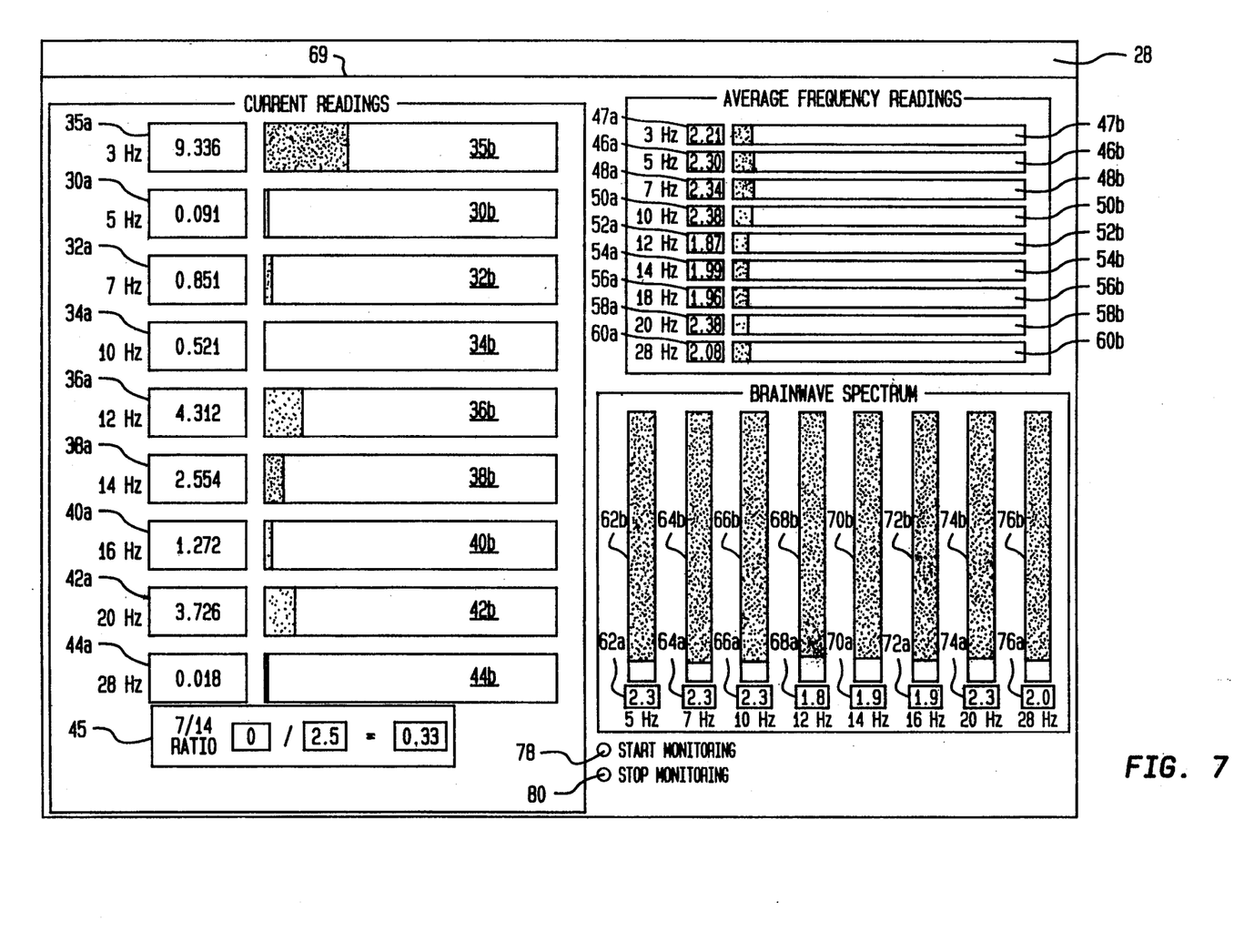
FIG. 7 is a front view of a display for a post traumatic stress disorder with a closed head injury condition.

FIG. 7 is a display 69 of a brainwave signature for a person with a post traumatic stress disorder. Low values are displayed in windows 32, 34, and 36 relating to bandwidths 7, 10 and 12 hz, respectively. The low values illustrate a slow down of the brain for a person with a stress disorder. A high value is shown in window 35 for a 3 hz bandwidth. Displays 61, 63, 65, 67 and 69 are displays of actual monitoring of a person with system 10.

Person 12 can be trained with EEG biofeedback system 10 by having a trainer monitor the brainwave signatures and give verbal feedback to the client relative to the observed brainwave signature. For example, after a patient is asked to think about a cognitive state a resulting brainwave signature is displayed, for example as shown in display 61. If patient 12 strays from thinking about the desired cognitive state (i.e., daydreaming or thinking about tonight's dinner party) a surge of energy in one or more bandwidths will occur and the displayed brainwave signature will be altered. At this time, the trainer can verbally guide patient 12 back to the desired brainwave signature.

CD sound system 104 can also be used to train person 12. A detected bandwidth can be chosen to be reinforced by sounds from sound system 104. For example, for the condition of "heavy hands" the 14 hz bandwidth can be chosen with biofeedback software 102 to be monitored by sound system 104. A music score begins playing as patient 12 is monitored. The loudness of the music will increase when an increased 14 hertz bandwidth is detected. If the loudness of the music decreases, person 12 is alerted that the concentration on the condition of "heavy hands" has diminished. The other patient 12 can concentrate on the "heavy hands" condition to increase the loudness of the music. An individual music score can be used for each desired bandwidth to be monitored.

The present invention has the advantage of monitoring bioelectric signals in a continuous spectrum in the range of about 0 to about 90 hertz. A brainwave signature corresponding to up to a 1 hertz window as bandwidths of interest can be displayed on a computer display for easily and accurately monitoring the cognitive state of the person being monitored. A person can be expeditiously trained with verbal or musical feedback related to the displayed brainwave signature.

While the invention has been described with reference to the preferred embodiment, this description is not intended to be limiting. It will be appreciated by those of ordinary skill in the art that modifications may be made without departing from the spirit and scope of the invention.

I claim:

1. An apparatus for monitoring a brainwave signature of a cognitive state of a person comprising:
    detecting means for detecting a bioelectric EEG signal from said person;
    amplifying means for amplifying said detected bioelectric EEG signal, said amplified bioelectric signal including a set of bandwidths, each of said bandwidths having a range of one hertz or less around a selected frequency;
    digital signal processing means for processing said set of bandwidths, said signal processing means including performing fast Fourier transforms on said bandwidths for determining respective amplitudes for each of said bandwidths in said set of bandwidths; and
    display means for displaying said respective amplitudes in respective windows of a computer display;
    wherein said brainwave signature of said cognitive state of said person is displayed as said respective amplitudes.

2. The apparatus of claim 1 further comprising:
    storage means in said computer for storing said brainwave signature.

3. The apparatus of claim 2 wherein said brainwave signature is displayed in real time.

4. The apparatus of claim 3 wherein said bioelectric signal is detected at a rate of 8,000 times per second.

5. The apparatus of claim 4 wherein the detected bioelectric signal is amplified by a factor of about 100.

6. The apparatus of claim 5 further comprising:
    sound means, said sound means including a respective music score for each of said bandwidths, said sound means increasing the loudness of said respective music score in response to an increase in said amplitude of said bandwidths.

7. The apparatus of claim 1 wherein one of said selected frequencies is 28 Hz.

8. The apparatus of claim 1 wherein three of said selected frequencies are 7, 10 and 16 Hz.

9. The apparatus of claim 1 wherein four of said selected frequencies are 7, 10, 16 and 28 Hz.

10. The apparatus of claim 1 wherein three of said selected frequencies are 7, 10 and 12 Hz.

11. A method for monitoring a brainwave signature of a cognitive state of a person comprising the steps of:
    detecting a bioelectric EEG signal from said person;
    amplifying said detected bioelectric EEG signal, said amplified bioelectric signal including a set of bandwidths, each of said bandwidths having a range of one hertz or less around a selected frequency;
    processing said set of bandwidths, said processing step including performing a fast Fourier transforms on said bandwidths in a digital computer for determining respective amplitudes for each of said bandwidths in said set of bandwidths; and
    displaying said respective amplitudes in respective windows of a computer display,
    wherein said brainwave signature of said cognitive state of said person is displayed as said respective amplitudes.

12. The method of claim 11 further comprising the step of:
    storing said brainwave signatures in a computer storage means.

* * * * *